United States Patent [19]

Bugaut et al.

[11] 4,259,261
[45] Mar. 31, 1981

[54] METAPHENYLENEDIAMINES

[75] Inventors: Andree Bugaut, Boulogne; Jean-Jacques Vandenbossche, Aulnay, both of France

[73] Assignee: L'Oreal, Paris, France

[21] Appl. No.: 22,615

[22] Filed: Mar. 21, 1979

Related U.S. Application Data

[63] Continuation-in-part of Ser. No. 826,069, Aug. 19, 1977, abandoned, which is a continuation-in-part of Ser. No. 722,819, Sep. 13, 1976, Pat. No. 4,125,367.

[30] Foreign Application Priority Data

Aug. 20, 1976 [FR] France ................ 76 25387

[51] Int. Cl.³ ............ C07C 91/40; C07C 91/42; C07C 93/14
[52] U.S. Cl. .............. 564/99; 260/163; 260/164; 564/47; 564/220; 564/441; 564/443
[58] Field of Search ......... 260/556 B, 556 A, 562 A, 260/575

[56] References Cited

U.S. PATENT DOCUMENTS

| | | | |
|---|---|---|---|
| 2,592,364 | 4/1952 | Weissberger et al. | 260/556 A |
| 2,921,961 | 1/1960 | Müller et al. | 260/575 X |
| 3,184,387 | 5/1965 | Seemuller | 260/575 X |
| 3,666,812 | 5/1972 | Kalopissis et al. | 260/575 X |
| 3,904,690 | 9/1975 | Kalopissis et al. | 260/556 B |
| 3,953,510 | 4/1976 | Smith et al. | 260/575 X |
| 4,005,143 | 1/1977 | Bohm et al. | 260/575 |
| 4,125,367 | 11/1978 | Bugaut et al. | 260/578 X |
| 4,152,112 | 5/1979 | Bugaut et al. | 260/575 X |
| 4,171,203 | 10/1979 | Rose et al. | 260/575 X |

Primary Examiner—Helen M. S. Sneed
Attorney, Agent, or Firm—Brisebois & Kruger

[57] ABSTRACT

Couplers having the general formula (I):

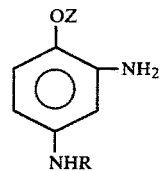

or the acid salts thereof in which formula
R is either
 (a) hydrogen or
 (b) a $C_1$–$C_3$ alkyl or
 (c) a $C_1$–$C_3$ hydroxyalkyl, and
Z is either
 (a) hydroxyalkyl, or
 (b) alkoxyalkyl in which the alkoxy group contains 1 to 2 carbon atoms, or
 (c) mesylaminoalkyl, or
 (d) acetylaminoalkyl, or
 (e) ureidoalkyl, or
 (f) carbethoxyaminoalkyl
the alkyl groups in the radicals constituting Z comprising from 2 to 3 carbon atoms and
Z is not hydroxyethyl when R is hydrogen.

These couplers form dyeing compositions when mixed with an oxidation base consisting of a paraphenylenediamine having the general formula:

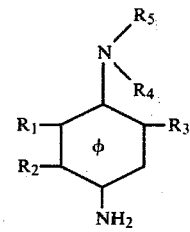

1 Claim, No Drawings

METAPHENYLENEDIAMINES

RELATED APPLICATIONS

This application is a continuation-in-part of application Ser. No. 826,069 filed Aug. 19, 1977, now abandoned which in turn is a continuation-in-part of Ser. No. 722,819, filed Sept. 13, 1976 (now U.S. Pat. No. 4,125,367).

BACKGROUND

In the field of dyeing keratinic fibers, hair and furs, the metaphenylenediamines play an important role which has been known for a long time. They form part of the class of compounds currently called "couplers". The couplers, in association with the paraphenylenediamines or the paraaminophenols—compounds called oxidation bases—produce in an alkaline oxidizing medium colored indamines, indoanilines or indophenols.

The association of the metaphenylenediamines with the paraphenylenediamines in an oxidizing alkaline atmosphere, and in particular in the presence of hydrogen peroxide, produce indamines capable of imparting to keratinic fibers very strong blue colors.

Moreover, the metaphenylenediamines associated with the paraaminophenols produce in an oxidizing alkaline atmosphere, indoanilines, which impart to keratinic fibers more or less purple-red colorations.

The metaphenylenediamines thus play, when considered as couplers, a double role in capillary dyeing: Contribution of blue and red, that is to say contribution of two fundamental colors which are indispensable to obtain not only blacks and greys, but also burnt or copper chestnuts.

Despite its important role this category of couplers is presently restricted in practice to a very limited number of compounds. This very limited number is explained by the fact that one may only keep for capillary dyeing on the one hand those beneficial compounds of a good innocuousness, and on the other hand the compounds permitting to obtain dyes of good qualities, that is to say, which do not change with time, in particular neither under light, nor inclement weather. By way of example, metatoluylene diamine is not satisfactory for reasons of non-innocuousness, while 1-methyl-2-amino-N-methyl-4-amino benzene, 2-amino-N-methyl-4-amino anisole, 2-amino-4-amino-N-methyl anisole, 2-amino-N-β-hydroxyethyl 4-amino anisole, 1-methyl 2-amino-N-β-hydroxyethyl-4-amino benzene lead to shades which are unstable with time, both in darkness and in the light. This instability is due principally to the ready cyclization into azinic molecules of the indoamines or indoanilines formed in situ during the oxidation dyeing, the azines formed then undergoing rapid photochemical degradation in the light.

THE PRESENT INVENTION

The present invention relates to new chemical compounds which are capable of functioning as couplers usable in hair dyeing compositions. The compounds according to the present invention are particularly usable in capillary dyeing because they combine a very good innocuousness with the dyeing qualities of a good coupler.

More specifically, the present invention involves chemical compounds of the general formula:

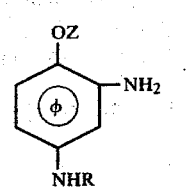

or the acid salts thereof in which formula
R is either
  (a) hydrogen or
  (b) a $C_1$-$C_3$ alkyl or
  (c) a $C_1$-$C_3$ hydroxyalkyl, and
Z is either
  (a) hydroxylakyl, or
  (b) alkoxyalkyl in which the alkoxy group contains 1 to 2 carbon atoms, or
  (c) mesylaminoalkyl, or
  (d) acetylaminoalkyl, or
  (e) ureidoakyl, or
  (f) carbethoxyaminoalkyl
  the alkyl groups in the radicals constituting Z comprising from 2 to 3 carbon atoms, and
  Z is not hydroxyethyl when R is hydrogen.

The compounds of the present invention can be used to form a dyeing composition for keratinic fibers and in particular for hair, said composition containing, in aqueous solution, at least one oxidation base that contains as a coupler, at least one compound of formula (I).

With the greater part of the paraphenylenediamines, in an alkaline oxidizing medium, the compounds of formula (I) impart to the hair strong blue colorations, more or less rich in green or in purple, resistant to the light, to bad weather, and to shampooing.

In a general way, in the dyeing composition containing the compounds of the present invention one may use as oxidation bases the paraphenylenediamines of the general formula (II):

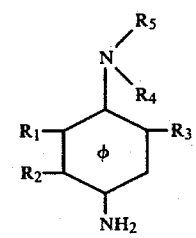

or the corresponding acid salts; in which $R_1$, $R_2$ and $R_3$ are identical or different and represent hydrogen, alkyl having 1 to 2 carbon atoms or alkoxy having 1 to 2 carbon atoms, $R_4$ and $R_5$ are identical or different and represent hydrogen, alkyl, hydroxyalkyl, alkoxyalkyl, in which the alkoxy group comprises 1 to 2 carbon atoms, carbamylalkyl, mesylaminoalkyl, acetylaminoalkyl, ureidoalkyl, carbethoxyaminoalkyl, the alkyl groups in $R_4$ and $R_5$ having 1 to 3 carbon atoms, with the reservation that $R_1$ or $R_3$ represent hydrogen when $R_4$ and $R_5$ do not represent hydrogen.

It should be noted however, that the paraphenylenediamines having a chlorine or fluorine atom on the ring yield with the compounds (I) violet colorations, which rapidly lose their chromaticity in the light. This is the case, for example, with 3-chloro-4-amino-N-β-hydroxyethyl aniline or 3-fluoro-4-amino-N-β-hydroxyethyl aniline.

To illustrate the invention we hereafter describe by way of purely illustrative and non-limiting examples, the preparation and use of the following specific compounds under formula (I):

1. Dihydrochloride of (2-amino-4-N-methylamino) phenoxyethanol.
2. Dihydrochloride of (2,4-diamino) phenylmethoxyethylether.
3. Dihydrochloride of (2,4-diamino) phenylmesylaminoethylether.

These three compounds give, in particular, blue colorations of very good stability with the following oxidation bases: paraphenylenediamine, paratoluylenediamine, 2-methyl 5-methoxy paraphenylenediamine, 2,6-dimethyl-3-methoxy paraphenylenediamine, 2,6-dimethyl paraphenylenediamine, 4-amino-N-methoxyethyl aniline, 4-amino-N,N-ethyl-carbamylmethyl aniline and 4-amino-N,N-di-$\beta$-hydroxyethyl aniline.

A certain number of compounds of formula (I) offer, from the dyeing point of view, the supplemental advantage of being able to also give stable reds when they are associated with paraaminophenol or 2-methyl-4-amino phenol. The dyeing compositions containing these compounds may then contain at the same time paraphenylene diamines and paraaminophenols.

For the other compounds of formula (I) which do not offer this supplementary advantage, one may in order to provide the red and violet necessary to the formulation of a capillary dyeing composition, add to the dyeing compositions containing them in addition to the paraphenylenediamines of formula (II) on the one hand leuco derivatives of indoanilines or indophenols such as: the 4,4'-dihydroxy-2-amino-5-methyl diphenylamine, 4,4'-dihydroxy-2-amino-N-$\beta$-hydroxyethyl-5-methyl-2'-chloro diphenylamine, 2,4'-diamino-4-hydroxy-5-methyl diphenylamine and on the other hand direct dyes such as, for example, 3-nitro-4-amino-N-$\beta$-hydroxyethyl phenol, 2-$\beta$-hydroxyethyl-amino-5-nitro anisole.

Dyeing compositions containing the compounds of the present invention may also contain in addition to the coupler or couplers of the formula (I) and the oxidation base or bases associated therewith, the following products taken singly or in combination:

1. Other known couplers, for example, resorcin, metaaminophenol, 2-methyl-5-amino phenol, 2-methyl-5-amino-N-$\beta$-hydroxyethyl phenol, 6-hydroxy benzomorpholine, 2,6-dimethyl-5-acethyl-amino phenol, 2-methyl-5-carbethoxyamino phenol, 2-methoxy-5-carbethoxyamino phenol, 2-methyl-5-ureido phenol;
2. Polyaminophenols, monoaminodiphenols, diaminodiphenols, polyphenols such as trihydroxybenzene;
3. Leucoderivatives of indoaniline or indophenols;
4. Direct dyes and preferably nitrated dyes of the benzene series such as 1-amino-N,N-di-$\beta$-hydroxyethyl-3-nitro-4-amino N'-methyl benzene, 1-amino-N,N-methyl-$\beta$-hydroxyethyl-3-nitro-4-amino-N'-$\beta$-hydroxyethyl benzene, 1-amino-N,N-methyl-$\beta$-hydroxyethyl-3-nitro-4-amino-N'-methyl benzene, 3-nitro-4-amino-N-$\beta$-hydroxyethyl anisole, 3-nitro-4-amino-N-$\beta$-hydroxyethyl phenol, (3-nitro-4-amino) phenoxyethanol, (3-nitro-4-amino-N-methyl) phenoxyethanol, 2-amino-$\beta$-hydroxyethyl-5-nitro anisole;
5. Various usual additives such as penetrating agents, foaming agents, thickening agents, anti-oxidizing agents, alkalizing agents, perfumes, sequestrating agents, and film forming products.

The pH of the dyeing compositions described above usually have a basic pH, for example between 8 and 11.5. We prefer a pH between about 9 and 10. Among the alkalizing agents which may be used, there can be mentioned ammonia, the alkyl amines, the alkanolamines, the hydroxides of sodium or potassium, and the carbonates of sodium, potassium or ammonium.

We may also add to the dye composition hydrosoluble anionic, cationic, non-ionic, or amphoteric surface-active agents. Among the surface active agents particularly useful there may be mentioned the alkyl benzene sulfonates, the alkylnaphthalene sulfonates, the sulfates, ether sulfates and sulfonates of fatty alcohols, quaternary ammonium salts, such as triethyl cetylammonium bromide, cetyl pyridinium bromide, the diethanolamides of fatty acids, the acids and the polyoxyethylenated alcohols and the polyoxyethylenated alkylphenols. Preferably, the surface active agents are present in the dyeing composition in a proportion between about 0.5 and 30% by weight, and preferably between about 4 and 25% by weight.

One may also add to the dye composition organic solvents to solubilize the compounds which are not sufficiently soluble in water. Among the solvents which may advantageously be used one may mention by way of example ethanol, isopropanol, glycerin, glycols like butyl glycol, ethylene glycol, propylene glycol, monoethylether, and monomethylether of diethylene glycol and analogous products. The solvents may advantageously be present in the composition in an amount ranging from 1 to 40% by weight and preferably between 5 and 30% by weight.

The thickening products which may be added to the dye composition may be sodium alginate, gum arabic, cellulose derivatives such as methylecullulose, hydroxyethylcellulose, hydroxypropyl methylcellulose, the sodium salt of carboxymethylcellulose, or polymers of acrylic acid. One may also use mineral thickening agents such as bentonite. Preferably the thickening agents are present in an amount between 0.5 and 5% by weight based on the total weight of the composition and preferably between 0.5 and 3% by weight.

The antioxidizing agents which one may add to the dye composition may be sodium sulfite, thioglycolic acid, the acid sulfite of sodium, ascorbic acid, or hydroquinone. The anti-oxidizing agents may be present in the composition in an amount between 0.05 and 1% by weight based on the total weight of the composition.

The dyeing composition may contain oxidizing agents such as hydrogen peroxide, urea peroxide, or the persalts such as ammonium persulfate.

In a general way, the compounds of formula (I) are present in the dyeing composition in an amount between 0.001 and 2.5% by weight based on the total weight of the composition.

The dyeing composition may be in the form of a liquid solution, a paste, a cream or gel, or any other appropriate form for bringing about a dyeing of keratinic fibers.

The compounds of formulas (I) may be easily prepared from compounds described in French patent application Nos. 74 36651 filed Nov. 5, 1974 and 76 12985 filed Apr. 30, 1976 and which are incorporated herein by reference.

Beginning with these benzene compounds nitrated in the meta position with respect to the amine group, it suffices to bring about a reduction to transform the nitro group into an amine group and possibly then effectuate the acid hydrolysis in the case in which the starting products comprises an acetylated amine function.

In order that the objectives of the present invention may be better understood, there will hereafter be described, purely by way of illustrative and non-limiting examples, the preparation of several compounds of formula (I) and the use of these compounds in dyeing compositions.

EXAMPLE 1

Preparation of dihydrochloride of (2-amino 4-N-methylamino) phenoxyethanol

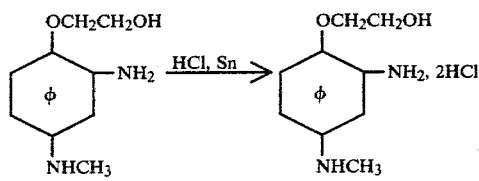

The starting compound is described in Example 5 of French Patent Application No. 74-36651 filed Nov. 5, 1974.

In 60 ml of hydrochloric acid (density=1.19 at 75° C.) one adds simultaneously, little by little, under agitation 0.05 mols (10.6 g) of (2-nitro 4-amino-N-methyl) phenoxyethanol and 14.3 g of tin powder. After completion of the additions, one continues the agitation for 15 minutes at 90° C. The reaction mixture is drained hot. Filtrate is evaporated until dry under a vacuum. The residue is dissolved in 300 ml of water and the tin is precipitated in the form of the sulfide by bubbling with hydrogen sulfite. It is filtered. The filtrate is concentrated to 15 ml under a vacuum. The concentrated solution is cooled to −10° C. The dihydrochloride of the expected product crystallizes. It is drained, washed with very little ice water and then vacuum dried. It melts with decomposition 26 225° C. The analysis of the product gives the following results:

|      | Calculated for $C_9H_{16}N_2O_2Cl_2$ | Found |
| --- | --- | --- |
| C % | 42.35 | 42.08 |
| H % | 6.27 | 6.45 |
| N % | 10.98 | 10.77 |
| Cl % | 27.84 | 27.73 |

EXAMPLE 2

Preparation of dihydrochloride of (2,4-diamino) phenyl-β-methoxyethylether

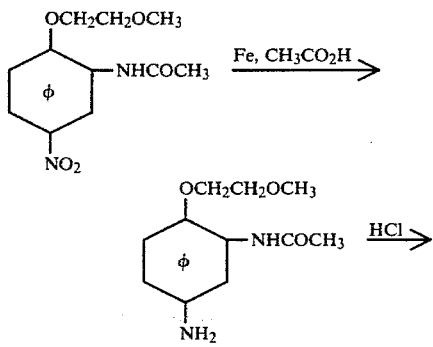

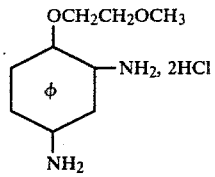

First Step

Preparation of (2-acetylamino 4-amino) phenyl β-methoxyethylether

To 100 ml of water to which 4 ml of acetic acid has been added and which has already been heated to 90° C., one adds 13 g of powdered iron and, little by little, under agitation, 0.078 mol (20 g) of 2-acetylamino-4-nitro) phenyl-β-methoxy-ethylether (product described in the first step of Example 8 of French Pat. No. 76-12985 filed Apr. 30, 1976, in the name of the applicant). The addition being terminated, one maintains the reaction mixture in the boiling water bath for 30 minutes. It is filtered hot. After the addition of sodium chloride to the filtrate, the expected product precipitates by salting out. It is drained, washed with very little ice water. It melts at 130° C.

Second Step

Preparation of dihydrochloride of (2,4-diamino) phenyl-β-methoxyethylether 0.067 mol (15 g) of 2-acetylamino 4-amino) phenyl-β-methoxyethylether is introduced into 30 ml of 36% hydrochloric acid. One heats 30 minutes in the boiling water bath. After cooling the dihydrochloride of the expected product crystallizes. It is drained, recrystalized in alcohol, and vacuum dried. The product melts with decomposition at 215° C.

The analyis gives the following results:

|      | Calculated for $C_9H_{16}N_2O_2Cl_2$ | Found |
| --- | --- | --- |
| C % | 42.35 | 42.47 |
| H % | 6.27 | 6.34 |
| N % | 10.98 | 10.85 |
| Cl % | 27.84 | 27.83 |

EXAMPLE 3

Preparation of dihydrochloride of (2,4-diamino) phenyl-mesylaminoethylether

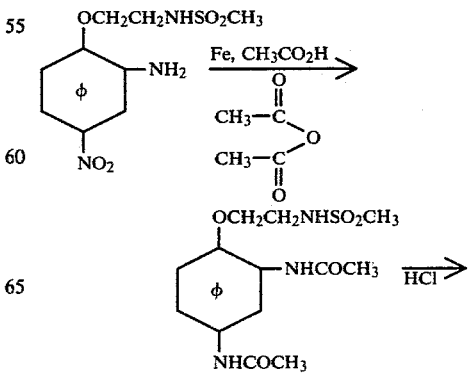

-continued

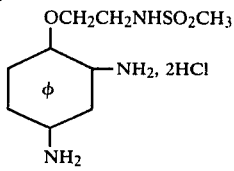

First Step

Preparation of (2,4-diacetylamino)-phenyl-mesylaminoethylether

Into 20 ml of water to which 2 ml of acetic acid has been added and which has been brought to 90° C., one adds 3.5 g of powdered iron and, little by little, under agitation, 0.02 mol (5.5 g) of (4-nitro-6-amino) phenyl mesylaminoethylether (product described in Example 12 of French Pat. No. 76-12985. The reflux is maintained under agitation for 30 minutes. It is drained while boiling and the precipitate washed in boiling water. 6 ml of acetic anhydride is added to the filtrate and the reaction medium heated for several minutes in a boiling water bath. After cooling the expected product crystallizes. It is drained, washed with water, vacuum dried. It melts at 191° C.

Second Step

Preparation of dihydrochloride of (2,4-diamino) phenyl-mesylaminoethylether One heats for 45 minutes in a boiling water bath 0.017 mol (5.6 g) of (2,4-diacetylamino) phenyl-mesylaminoethylether in 14 ml of hydrochloric acid at 36%. After cooling, the dihydrochloride of the expected product precipitates in crystallized form. The product is drained, recrystallized in alcohol and vacuum dried at 60° C.

Analysis gives the following results:

|  | Calculated for $C_9H_{17}N_3O_3S\ Cl_2$ | Found |
|---|---|---|
| C % | 33.96 | 33.93 |
| H % | 5.38 | 5.45 |
| N % | 13.20 | 13.12 |
| Cl % | 22.28 | 22.10 |
| S % | 10.08 | 10.15 |

EXAMPLE 4

The following dyeing composition is prepared:

| | |
|---|---|
| Compound of example 2 | 0.127 g |
| 4-amino-N-ethyl-N-carbamylmethyl aniline | 0.193 g |
| Butylglycol | 20 g |
| Lauric alcohol having 10.5 mols of ethylene oxide | 8 g |
| Ammonia at 22° B. | 4.5 g |
| Water, q.s. | 100 g |

The pH is 10.3.

At the moment of use one adds 35 g of hydrogen peroxide at 20 volumes. This mixture applied to 95% naturally white hair for 20 minutes at ambient temperature imparts thereto, after rinsing and shampooing, a sky blue coloration.

EXAMPLE 5

The following dyeing composition is prepared:

| | |
|---|---|
| Compound of example 3 | 0.016 g |
| Sulfate of 3-methyl-4-methylethylamino aniline | 0.028 g |
| Carboxymethylcellulose | 5 g |
| Water, q.s. | 100 g |
| Ammonia at 22° B. | 6 g |

The pH is equal to 11.

At the moment of use 15 g of hydrogen peroxide at 20 volumes is added.

This mixture applied for 25 minutes at 30° C. to bleached hair imparts thereto, after rinsing and shampooing, a sky blue coloration.

EXAMPLE 6

The following dyeing composition is prepared:

| | |
|---|---|
| Compound of example 2 | 0.255 g |
| Dihydrochloride of 4-amino-N-methyl aniline | 0.195 g |
| Oleic alcohol oxyethylenated with 2 mols of ethylene oxide | 3 g |
| Oleic alcohol oxyethylenated with 4 mols of ethylene oxice | 4.4 g |
| Ammonia at 22° B. | 6 g |
| Water, q.s. | 100 g |

The pH is equal to 10.

At the moment of use 25 g of hydrogen peroxide at 20 volumes is added.

This mixture is applied for 10 minutes at 30° C. to 90% naturally white hair imparts thereto, after rinsing and shampooing, a royal blue coloration.

EXAMPLE 7

The following dyeing composition is prepared:

| | |
|---|---|
| Compound of example 3 | 0.954 g |
| Dihydrochloride of 2,6-dimethyl-3-methoxy paraphenylenediamine | 1.43 g |
| Alkyl ammonium sulfate in $C_{12}$, $C_{14}$ (70% of $C_{12}$ and 30% of $C_{14}$) | 15 g |
| Lauric alcohols having 10.5 mols of ethylene oxide | 5 g |
| Ammonia at 22° B. | 10 g |
| Water, q.s. | 100 g |

The final pH is equal to 10.2.

At the moment of use, 75 g of hydrogen peroxide at 20 volumes is added. This mixture applied for 20 minutes at 25° C. to 95% naturally white hair imparts thereto, after rinsing and shampooing, a clear pure blue coloration.

EXAMPLE 8

The following dyeing composition is prepared:

| | |
|---|---|
| Compound of example 2 | 0.12 g |
| Trihydroxybenzene | 0.82 g |
| N-ethyl-4-amino-N-carbamylmethyl aniline | 2.6 g |
| 3-nitro-4-N-amino-$\beta$-hydroxyethyl phenol | 0.29 g |
| Alcohol at 96% | 20 g |
| Triethanolamine | 6 g |
| Water, q.s. | 100 g |

The pH is equal to 9.

At the moment of use 60 g of hydrogen peroxide at 20 volumes is added.

This mixture applied to bleached hair for 20 minutes at 20° C. imparts thereto, after rinsing and shampooing, a deep brown coloration having light violet glints.

EXAMPLE 9

The following dyeing composition is prepared:

| | |
|---|---|
| Compound of example 2 | 0.2 g |
| Dihydrochloride of 2-methyl-5-methoxy paraphenylenediamine | 0.2 g |
| 4-amino-N,N-β-hydroxyethyl aniline sulfate | 0.2 g |
| Metaaminophenol | 0.3 g |
| 6-hydroxy benzomorpholine | 0.1 g |
| 3-nitro-4-amino-N-β-hydroxyethyl anisole | 0.2 g |
| 4-mino-N-methyl phenol sulfate | 0.4 g |
| Monomethyl ester of diethyleneglycol | 9 g |
| Ammonia at 22° B. | 10 g |
| Water, q.s. | 100 g |

The pH is equal to 10.7.

At the moment of use 100 g of hydrogen peroxide at 20 volumes is added.

This mixture applied for 30 minutes at 20° C. to bleached hair imparts thereto, after rinsing and shampooing, a very deep reddish chestnut coloration.

EXAMPLE 10

The following dyeing composition is prepared:

| | |
|---|---|
| Compound of example 3 | 0.105 g |
| Resorcin | 15 g |
| Dihydrochloride of 2,6-dimethyl-5-methoxy paraphenylenediamine | 0.3 g |
| 1-phenyl-3-methyl pyrazolone | 0.1 g |
| 3-nitro-4-amino-N-β-hydroxyethyl phenol | 0.2 g |
| Hydrochloride of (2-amino-4-nitro) phenoxyethanol | 0.25 g |
| 4,4'-dihydroxy-2-amino-5-methyl diphenylamine | 0.4 g |
| Butylglycol | 15 g |
| Nonylphenol having 4 mols of ethylene oxide | 8 g |
| Nonylphenol having 9 mols of ethylene oxide | 9 g |
| Ammonia at 22° B. | 5 g |
| Water, q.s. | 100 g |

The pH is equal to 9.8.

At the moment of use, 80 g of hydrogen peroxide at 20 volumes is added.

This mixture applied for 25 minutes at 20° C. to bleached hair imparts thereto, after rinsing and shampooing, a clear golden chestnut coloration.

EXAMPLE 11

The following dyeing composition is prepared:

| | |
|---|---|
| Compound of example 2 | 0.13 g |
| 3-fluoro-4-amino-N-hydroxyethyl aniline sulfate | 0.22 g |
| Trihydrochloride of 4-amino-N-diethyl-2,6-diamino phenol | 0.12 g |
| N[(4-hydroxy) phenyl]-2-methyl-5-amino benzoquinone imine | 0.70 g |
| Butylglycol | 5 g |
| Lauric alcohol oxyethylenated with 10.5 mols of ethylene oxide | 5 g |
| Triethanolamine | 1.1 g |
| Water, q.s. | 100 g |

At the moment of use, 10 g of urea peroxide is added in 100 g of water.

This mixture applied for 25 minutes at 20° C. to bleached hair imparts thereto, after rinsing and shampooing, a burnt beige grey coloration.

EXAMPLE 12

The following dyeing composition is prepared:

| | |
|---|---|
| Compound of example 3 | 0.075 g |
| Dihydrochloride of (2,4-diamino)phenoxyethanol | 0.025 g |
| Resorcin | 0.11 g |
| m-amino phenol | 0.1 g |
| 4-amino-N-phenol sulfate | 0.2 g |
| 4-amino-N-β-methoxyethyl aniline sulfate | 0.3 g |
| 3-nitro-4-amino phenoxyethanol | 0.3 g |
| 2,4'-diamino-4-hydroxy-5-methyl diphenylamine | 0.25 g |
| 2-amino-N-β-hydroxyethyl-5-nitro-anisole | 0.125 g |
| Hydroquinone | 0.0325 g |
| | 3.33 g |
| $R\left(-OCH_2\,CH-\atop CH_2OH\right)_2 OH$ (R being an oleyl radical) | |
| $R\left(-OCH_2-CH-\atop CH_2OH\right)_4 OH$ (R being an oleyl radical) | 4.95 g |
| Propyleneglycol | 6.6 g |
| Ammonia at 22° B. | 10 g |
| Water, q.s. | 100 g |

The pH is equal to 10.3.

At the moment of use 75 g of hydrogen peroxide at 20 volumes is added.

This mixture applied for 20 minutes at ambient temperature to 95% naturally white hair imparts thereto, after rinsing and shampooing, a bronze coloration.

EXAMPLE 13

The following dyeing composition is prepared:

| | |
|---|---|
| Dye of example 1 | 0.14 g |
| Dihydrochloride of 2,6-dimethyl-3-methoxy paraphenylenediamine | 0.20 g |
| Trihydrochloride of 4-amino-N-diethyl-2,6-diamino phenol | 0.1 g |
| N[(4-hydroxy) phenyl]2-methyl-5-amino benzoquinone imine | 0.5 g |
| Butylglycol | 5 g |
| Lauric alcohol oxyethylenated with 10.5 mols of ethylene oxide | 5 g |
| Triethanolamine | 1.1 g |
| Water, q.s. | 100 g |

The pH is equal to 8.

10 g of urea peroxide in solution in 100 g of water is added at the moment of use.

This solution applied for 20 minutes at ambient temperature to bleached hair imparts thereto, after rinsing and shampooing, a deep grey coloration.

EXAMPLE 14

The following dyeing composition is prepared:

| | |
|---|---|
| Compound of example 1 | 0.20 g |
| Paraaminophenol | 0.60 g |
| 4-amino-N-β-methoxyethyl aniline sulfate | 0.325 g |
| Metaaminophenol | 0.44 g |
| (3-nitro-4-amino) phenoxyethanol | 0.25 g |
| Butylglycol | 20 g |
| Diethanolamides of fatty acids of copra | 7.4 g |
| Ammonia at 22° B. | 6 g |
| Water, q.s. | 100 g |

The pH is equal to 10.5.

At the moment of use 100 g of hydrogen peroxide at 20 volumes is added. This dyeing composition applied for 20 minutes at 25° C. to 95% naturally white hair imparts thereto, after rinsing and shampooing, a golden chestnut coloration.

EXAMPLE 15

The following dyeing composition is prepared:

| | |
|---|---|
| Compound of example 2 | 0.0012 g |
| 4-amino-N-β-methoxyethyl aniline sulfate | 0.00125 g |
| Butylglycol | 7.5 g |
| Product sold under the commercial name of "Carbopol 934" Polymer of acrylic acid (M.W. = 2-3 millions) manufactured by the Goodrich Chemical Co. | 3.37 g |
| Ammonia to 22° B. | 7.5 g |
| Water, q.s. | 100 g |

The pH is equal to 8.

At the moment of use, 15 g of hydrogen peroxide at 20 volumes is added. This composition applied for 30 minutes at 25° C. to bleached hair imparts thereto, after rinsing and shampooing, a clear blue coloration.

EXAMPLE 16

Preparation of dichlorohydrate of (2,4-diamino) phenoxypropanol.

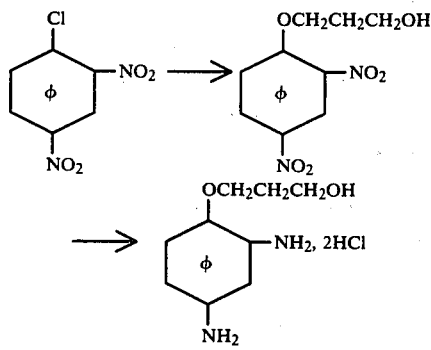

First Step

Preparation of (2,4-dinitro) phenoxypropanol

To a mixture of 0.2 mol (40.5 g) of 2,4-dinitro chlorobenzene and of 1.12 mol (81 cm$^3$) of 1,3-propanediol, heated to 90° C. is added in 30 minutes 1.1 mol (81 cm$^3$) of 1,3-propanediol in 20 cm$^3$ of 10 N sodium hydroxide.

After 45 minutes of heating at 90° C., the reactive medium is poured over 250 g of an ice/water mixture. The expected product crystallizes.

After recrystallization in the isopropyl alcohol/ether mixture, one obtains a product melting at 58° C.

Analysis yields the following results:

| | Calculated for $C_9H_{10}N_2O_6$ | Found |
|---|---|---|
| C % | 44.63 | 44.52 |
| H % | 4.13 | 4.42 |
| N % | 11.57 | 11.34 |

Second Step

Preparation of dichlorhydrate of (2,4-diamino) phenoxypropanol 0.039 mol (9.5 g) of (2,4-dinitro) phenoxypropanol in 30 cm$^3$ of absolute alcohol are reduced on Pd/C at 10% in a bomb under 25 kg of pressure of hydrogen at 70° C. for 1 hour.

After cooling, it is filtered on 0.117 mol (17 cm$^3$) of hydrochloric alcohol (i.e. ethanol into which is bubbled gaseous hydrochloric acid until saturation, e.g. 3-4 hours).

The expected dichlorohydrate crystallizes. The product is dried, washed with alcohol, then with ether and dried in a vacuum. It melts with decomposition at 158° C. Analysis yields the following results:

| | Calculated for $C_9H_{16}N_2O_2Cl_2$ | Found |
|---|---|---|
| C % | 42.35 | 42.20 |
| H % | 6.27 | 6.42 |
| N % | 10.98 | 11.13 |
| Cl % | 27.84 | (27.92) |
| | | (27.84) |

EXAMPLE 17

The following dyeing composition is prepared:

| | |
|---|---|
| Dichlorhydrate of (2,4-diamino) phenoxypropanol | 0.637 g |
| Paraphenylenediamine | 0.270 g |
| Sodium laurylsulfate with 2 mols of ethylene oxide | 20 g |
| Tetraacetic ethylenediamine acid | 0.2 g |
| Sodium bisulfite in solution d = 1.32 | 1 g |
| 20% ammonia | 10 g |
| Water q.s.p. | 100 g |

The pH equals 10.5.

At the time of use, 100 g of hydrogen peroxide at 20 volumes is added. This mixture applied for 20 minutes at 25° C. to naturally white hair at 90% gives it, after rinsing and shampooing, a marine blue color with purple highlights.

EXAMPLE 18

The following dyeing composition is prepared:

| | |
|---|---|
| Dichlorhydrate of (2,4-diamino) phenoxypropanol | 0.637 g |
| Paraminophenol | 0.272 g |
| Sodium laurylsulfate with 2 mols of ethylene oxide | 20 g |
| Tetraacetic ethylenediamine acid | 0.2 g |
| Sodium bisulfite in solution d = 1.32 | 1 g |
| 20% ammonia | 10 g |
| Water q.s.p. | 100 g |

The pH equals 10.5.

At the time of use, 100 g or H$_2$O$_2$ at 20 volumes is added. This mixture applied for 20 minutes at 25° C. to naturally white hair at 90% gives it, after rinsing and shampooing, a dark red, slightly purple, color.

EXAMPLE 19

Preparation of dichlorhydrate of (2,4-diamino)phenyl, β-acetylamino-ethylether

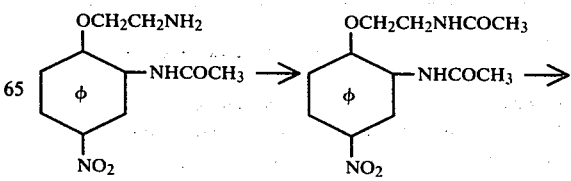

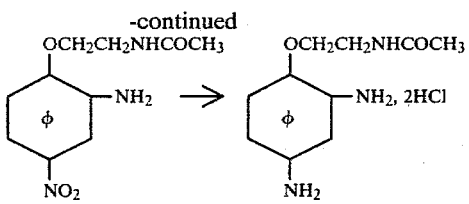

First Step

Preparation of (2-acetamino 4-nitro) phenyl,β-acetylaminoethylether 0.021 mol (2cm³) of acetic anhydride is added to the suspension of 0.0167 mol (4 g) of (2-acetamino 4-nitro) phenyl, β-amino-ethylether in 20 cm³ of dioxane. After 15 minutes of agitation at 50° C., it is chilled in an ice bath.

The product formed is dried, washed with petroleum ether and dried in a vacuum at 55° C.

It melts at 202°–203° C.

Second Step

Preparation of (2-amino 4-nitro) phenyl,β-acetaminoethylether 0.00817 mol (2.3 g) of (2-acetamino 4-nitro) phenyl, β-acetaminoethylether are heated for one hour in HCl (1 N).

After cooling, it is neutralized with NH₄OH. The expected product crystallizes. After recrystallization in alcohol, it melts at 125° C.

Elementary analysis yields the following results:

|   | Calculated for $C_{10}H_{13}N_3O_4$ | Found |
|---|---|---|
| C % | 50.20 | 50.39 |
| H % | 5.48 | 5.41 |
| N % | 17.57 | 17.59 |

Third Step

Preparation of dichlorohydrate of (2,4-diamino) phenyl,β-acetylaminoethylether 0.0079 mol (1.9 g) of (2-amino 4-nitro)-phenyl, β-acetylaminoethylether in 30 cm³ of absolute alcohol is reduced on Pd/C at 10%, under a hydrogen pressure of 30 kg at 60° C. for half an hour.

After cooling, it is percolated through 3 cm³ of hydrochloric alcohol (ethanol in which is bubbled gaseous hydrochloric acid until saturation, e.g. 3 or 4 hours). By dilution with ether, the expected product crystallizes. After centrifugal drying and then drying in a vacuum, it melts with decomposition starting at 270° C.

Theoretical mass calculated for $C_{10}H_{15}N_3O_2$, 2HCl:282.2

Molecular mass found by potentiometric titration in H₂O by NaOH N/10.

PM₁:281. 1st inflection
PM₂:287.5 2nd inflection

EXAMPLE 20

The following dyeing composition is prepared:

| | |
|---|---|
| Dichlorhydrate of (2,4-diamino) phenyl, β-acetaminoethylether | 0.706 g |
| Dichlorhydrate of paratoluylene diamine | 0.487 g |
| 2-Butoxy ethanol | 5 g |
| Lauric alcohol with 10.5% ethylene oxide | 5 g |
| Ammonia (22° Baumé) | 10 g |
| Water q.s.p. | 100 g |

The pH equals 10.3.

At the time of use, 100 g of hydrogen peroxide at 20 volumes is added. This mixture applied for 20 minutes at 20° C. to naturally white hair to 90% gives it, after rinsing and shampooing, a nice clear blue color.

EXAMPLE 21

Preparation of dichlorohydrate of [4-N(β-hydroxyethyl)-amino 2-amino] phenoxyethanol

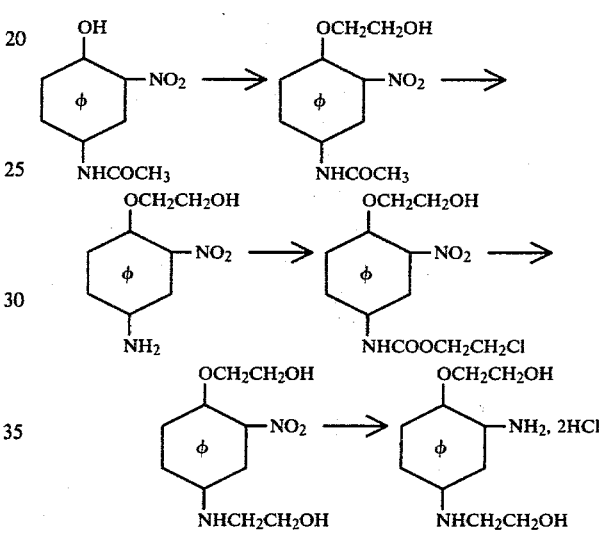

First Step

Preparation of (4-acetamino 2-nitro)phenoxyethanol 0.1 mol (19.6 g) of 4-acetamino 2-nitro phenol in 100 cm³ of dimethylformamide is heated to 80° C. Then 0.24 mol (16.8 g) of potassium hydroxide at 80% and 0.24 mol (30 g) of glycol bromhydrine are added by fractions during 4½ hours of heating in a boiling water bath.

The reactive medium is then poured on 300 g. of an ice water mixture. The expected product crystallizes. After filtration washing and drying, it melts at 169° C.

Second Step

Preparation of (4-amino 2-nitro)phenoxyethanol 0.106 mol of (4-acetamino 2-nitro) phenoxyethanol (25.5 g) is heated in a boiling water bath in 35 cm³ of HCl for 45 minutes.

By cooling, the chlorhydrate of the expected product precipitates. After filtration, it is added to 100 g of iced water and neutralized with NH₄OH. The expected product is filtrated washed and dried in a vacuum; it melts at 86° C.

Theoretical mass: 198

Molecular mass found by potentiometric titration in CH₃COOH by HClO₄ N/10: 204

Third Step

Preparation of [(3-nitro 4-β-hydroxyethoxy)phenyl] carbamate of β-chlorethyl 0.0605 mol (12 g) of (4-amino 2-nitro) phenoxyethanol is dissolved in 40 cm³ of dioxane. 0.033 mol (3.3 g) of calcium carbonate is added and the temperature is raised to about 90° C. During agitation, 0.066 mol (9.4 g) of chloroformiate of β-ethyl chloride is added. After this addition, the agitation is continued for 1½ hours at 90° C. The reactive medium is filtered while hot and 60 g of an ice water mixture is added.

The resulting product which has precipitated is filtrated. After washing and drying, it melts at 84° C.

Fourth Step

Preparation of [4-N-(β-hydroxyethyl)-amino 2-nitro] phenoxyethanol 0.0446 mol (13.6 g) of [(3-nitro 4-β-hydroxyethoxy)phenyl] carbamate of β-ethylchloride is added to 51 cm³ of NaOH 5 N. It is agitated for half an hour at 80° C. The reactive medium is cooled to 0° C. and neutralized with HCl. The resulting product is extracted with methyl-isobutyl-ketone. The solvent is driven out under reduced pressure. The resulting product is in the form of a red oil.

Fifth Step

Preparation of dichlorhydrate of [4-N-(β hydroxyethyl)-amino 2-amino] phenoxyethanol.

0.0392 mol (9.5 g) of [4-N-(β hydroxyethyl)-amino 2-nitro] phenoxyethanol in 30 cm³ of absolute alcohol is reduced on Pd/C at 10% in a bomb under 50 kg of pressure of $H_2$ for 45 minutes at 60° C.

After cooling it is percolated thru 0.096 mol (12 cm³) of hydrochloric alcohol.

The expected dichlorohydrate crystallizes. It is filtrated, washed, dried with ethyl ether, and dried in a vacuum at 55° C. It melts with decomposition at 223° C.

Theoretical mass calculated for $C_{10}H_{16}N_2O_3$ 2HCl: 285

Molecular mass obtained by potentiometric titration in water by NaOH N/10: 290.

EXAMPLE 22

The following dyeing mixture is prepared:

| | |
|---|---|
| Dichlorhydrate of [4-N-(β-hydroxyethyl) -amino 2-amino] phenoxyethanol | 0.427 g |
| | 0.276 g |
| Paraphenylenediamine | 0.270 g |
| Butoxy-2 ethanol | 5 g |
| Lauric alcohol at 10.5 mol of ethylene oxide | 5 g |
| Ammonia (22° Baume) | 10 g |
| Water q.s.p. | 100 g |

The pH equals 10.3.

At the time of use, 100 g of $H_2O_2$ at 20 volumes are added. This mixture applied for 25 minutes at 20° C. to naturally white hair at 90% gives it, after rinsing and shampooing, a deep violet blue color.

EXAMPLE 23

The following dyeing mixture is prepared:

| | |
|---|---|
| Dichlorhydrate of [4-N-(β-hydroxyethyl) -amino 2-amino] phenoxyethanol | 0.712 g |
| Paraphenylene diamine | 0.270 g |
| Sodium laurylsulfate with 2 mol of ethylene oxide | 20 g |
| Tetraacetic ethylenediamine acid | 0.2 g |
| Sodium bisulfite in solution d = 1.32 | 1 g |
| Ammonia (22° Baume) | 10 g |
| Water q.s.p. | 100 g |

The pH equals 10.4.

At the time of use, 100 g of hydrogen peroxide at 20 volumes are added. This mixture applied for 20 minutes at 20° C. to naturally white hair at 90% gives it, after rinsing and shampooing, a purplish blue-grey color.

EXAMPLE 24

Preparation of dichlorhydrate of (2,4-diamino) phenyl,β-ureidoethyl ether

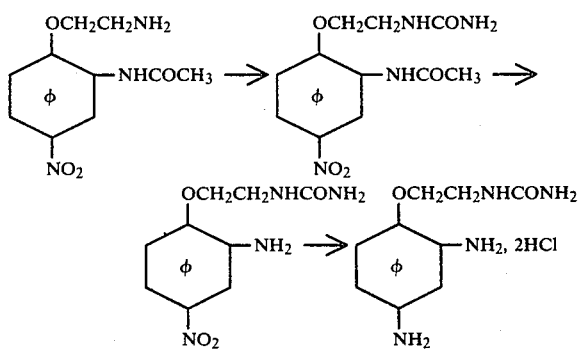

First Step

Preparation of (2-acetamino 4-nitro)phenyl,β-ureidoethyl ether

To 0.0209 mol (5 g) of (2-acetamino 4-nitro) phenyl,β-amino ethyl ether in 15 cm³ of water and 2.5 cm³ of HCl is added all at once 0.23 mol (1.86 g) of potassium cyanate in solution in 6 cm³ of water.

It is agitated for 3 hours at 40° C., then kept at room temperature for three days.

After filtration, washing first with 1 N HCl then with water, the expected product results, melting at 230°–231° C.

Second Step

Preparation of (2-amino 4-nitro)phenyl,β-ureidoethyl ether 0.007 mol (2 g) of (2-acetamino 4-nitro) phenyl, β-ureidoethyl ether is heated in 15 cm³ of 1 N HCl for 1 hour and 15 min. After cooling, the reactive mixture is diluted with 15 g of ice and neutralized with $NH_4OH$.

After filtration, washing with $H_2O$ and drying in a vacuum on $P_2O_5$, the expected product melts at 208° C.

Third Step

Preparation of dichlorhydrate of (2,4-diamino)phenyl β-ureidoethyl ether 0.00565 mol (1.35 g) of (2-amino 4-nitro) phenyl, β-ureido-ethyl ether in 5 cm³ of absolute alcohol is reduced on Pd/C at 10% in a bomb under 50 kg of hydrogen pressure for one hour at 60°–70° C. After cooling, it is filtered on 0.016 mol (2 cm³) of hydrochloric alcohol. After energetic agitation, the expected dichlorhydrate precipitates. After filtration washing with ether and drying, it melts with decomposition at 175° C.

Theoretical mass calculated for $C_9H_{14}N_4O_2$, 2HCl: 283

Molecular mass found by potentiometric titration in $H_2O$ by NaOH N/10: 298

EXAMPLE 25

The following dyeing composition is prepared:

| | |
|---|---|
| Dichlorhydrate of (2,4-diamino)phenyl, β-ureidoethyl ether | 0.340 g |
| Dichlorhydrate of paratoluylenediamine | 0.487 g |
| Sodium laurylsulfate wtih 2 mol of ethylene oxide | 20 g |
| Tetraacetic ethylenediamine | 0.2 g |
| Sodium bisulfite in solution of d = 1.32 | 1 g |
| Ammonia at 20% | 10 g |
| -continued | |
| Water q.s.p. | 100 g |

The pH equals 10.4.

At the time of use, 100 g of $H_2O_2$ at 20 volumes is added. The mixture applied for 25 minutes at 20° C. to white hair at 90% gives it after rinsing and shampooing a steel blue-grey color. What is claimed is:

1. Compounds having the formula:

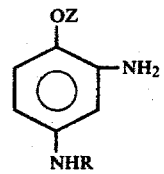

or the acid salts thereof in which formula R is hydrogen and Z is mesylaminoethyl.

* * * * *